US010492668B2

(12) United States Patent
Yoon et al.

(10) Patent No.: US 10,492,668 B2
(45) Date of Patent: Dec. 3, 2019

(54) ENDOSCOPE SYSTEM AND CONTROL METHOD THEREOF

(71) Applicant: Samsung Electronics Co., Ltd., Suwon-Si, Gyeonggi-Do (KR)

(72) Inventors: Suk June Yoon, Seoul (KR); No San Kwak, Suwon-si (KR); Kyung Shik Roh, Seongnam-si (KR); Sung Hwan Ahn, Seongnam-si (KR); Won Jun Hwang, Seoul (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 902 days.

(21) Appl. No.: 14/134,415

(22) Filed: Dec. 19, 2013

(65) Prior Publication Data
US 2014/0243596 A1   Aug. 28, 2014

(30) Foreign Application Priority Data

Feb. 28, 2013  (KR) .................. 10-2013-0022535

(51) Int. Cl.
*A61B 1/00*   (2006.01)
*A61B 1/31*   (2006.01)
*G06T 7/593*  (2017.01)

(52) U.S. Cl.
CPC ...... *A61B 1/00193* (2013.01); *A61B 1/00009* (2013.01); *A61B 1/31* (2013.01); *G06T 7/593* (2017.01); *G06T 2207/10012* (2013.01)

(58) Field of Classification Search
CPC ........ G06T 2207/10012; G06T 7/0075; A61B 1/00009; A61B 1/00193; A61B 1/31

(Continued)

(56) References Cited

U.S. PATENT DOCUMENTS 5,018,509 A * 5/1991 Suzuki ................ A61B 1/0005
                                             348/65
6,002,430 A * 12/1999 McCall .............. H04N 5/23238
                                             348/143

(Continued)

FOREIGN PATENT DOCUMENTS

EP    1006484 A2   6/2000
JP    2006-187385 A  7/2006

(Continued)

OTHER PUBLICATIONS

Yasugi Yagi, "Omnidirectional Sensing and Its Applications", Mar. 1999, vol. E82-D No. 3, pp. 568-579.*

(Continued)

*Primary Examiner* — Timothy J Neal
*Assistant Examiner* — Jae Woo
(74) *Attorney, Agent, or Firm* — Harness, Dickey & Pierce, P.L.C.

(57) ABSTRACT

Disclosed herein are an endoscope system and a control method thereof. The control method includes acquiring plural omnidirectional images of the surroundings of an endoscope using a stereo omnidirectional camera mounted on the endoscope, calculating distances between the endoscope and an object around the endoscope using the acquired plural omnidirectional images, and executing an operation to avoid collision between the endoscope and the object around the endoscope based on the calculated distances, thus facilitating safe operation of the endoscope.

14 Claims, 16 Drawing Sheets

(58) Field of Classification Search
USPC .......................................... 600/111, 117, 114
See application file for complete search history.

(56) References Cited

U.S. PATENT DOCUMENTS

| | | | | |
|---|---|---|---|---|
| 6,744,569 B2* | 6/2004 | Geng | ..................... | G03B 17/00 348/E13.014 |
| 8,211,009 B2* | 7/2012 | Tanaka | ................. | A61B 1/0051 600/109 |
| 8,212,862 B2* | 7/2012 | Kase | ................. | A61B 1/00147 348/68 |
| 8,480,568 B2* | 7/2013 | Tanaka | ............... | A61B 1/00039 600/117 |
| 8,795,157 B1* | 8/2014 | Yaron | ................ | A61B 1/00147 348/65 |
| 2003/0152897 A1* | 8/2003 | Geiger | .................... | G06T 15/00 434/262 |
| 2004/0024311 A1* | 2/2004 | Quaid, III | .............. | A61B 90/36 600/428 |
| 2004/0034282 A1 | 2/2004 | Quaid | | |
| 2004/0220478 A1 | 11/2004 | Wallace et al. | | |
| 2005/0010082 A1* | 1/2005 | Nishimura | ......... | A61B 1/00147 600/145 |
| 2008/0009674 A1* | 1/2008 | Yaron | ................... | G06T 19/003 600/117 |
| 2008/0075357 A1* | 3/2008 | Yoon | ................. | G06K 9/00791 382/153 |
| 2008/0232678 A1* | 9/2008 | Yoon | ................. | G06K 9/00791 382/153 |
| 2009/0022393 A1* | 1/2009 | Bar-Zohar | .............. | G06T 7/593 382/154 |
| 2009/0048482 A1* | 2/2009 | Hong | ....................... | A61B 1/04 600/103 |
| 2009/0054729 A1 | 2/2009 | Mori et al. | | |
| 2009/0149711 A1* | 6/2009 | Tanaka | ................. | A61B 1/0052 600/152 |
| 2009/0154769 A1* | 6/2009 | Yoon | ........................ | G06K 9/32 382/103 |
| 2009/0154791 A1* | 6/2009 | Yoon | ................... | G06K 9/00664 382/153 |
| 2009/0276092 A1* | 11/2009 | Yoon | ...................... | B25J 9/1666 700/245 |
| 2009/0292166 A1* | 11/2009 | Ito | ...................... | A61B 1/00009 600/109 |
| 2009/0292171 A1* | 11/2009 | Ito | ..................... | A61B 1/00009 600/111 |
| 2010/0040279 A1* | 2/2010 | Yoon | .................... | G05D 1/0251 382/153 |
| 2010/0168918 A1* | 7/2010 | Zhao | ...................... | B25J 9/1689 700/259 |
| 2012/0134537 A1* | 5/2012 | Yoon | ...................... | G06T 7/0075 382/103 |
| 2012/0209069 A1 | 8/2012 | Popovic et al. | | |
| 2013/0046137 A1 | 2/2013 | Zhao et al. | | |

FOREIGN PATENT DOCUMENTS

| | | |
|---|---|---|
| JP | 2010-220787 A | 10/2010 |
| KR | 2011-0072429 A | 6/2011 |
| WO | WO-2005077253 A1 | 8/2005 |

OTHER PUBLICATIONS

Office Action for corresponding Korean Application No. 10-2013-0022535 dated Jun. 19, 2019 and English translation.

* cited by examiner

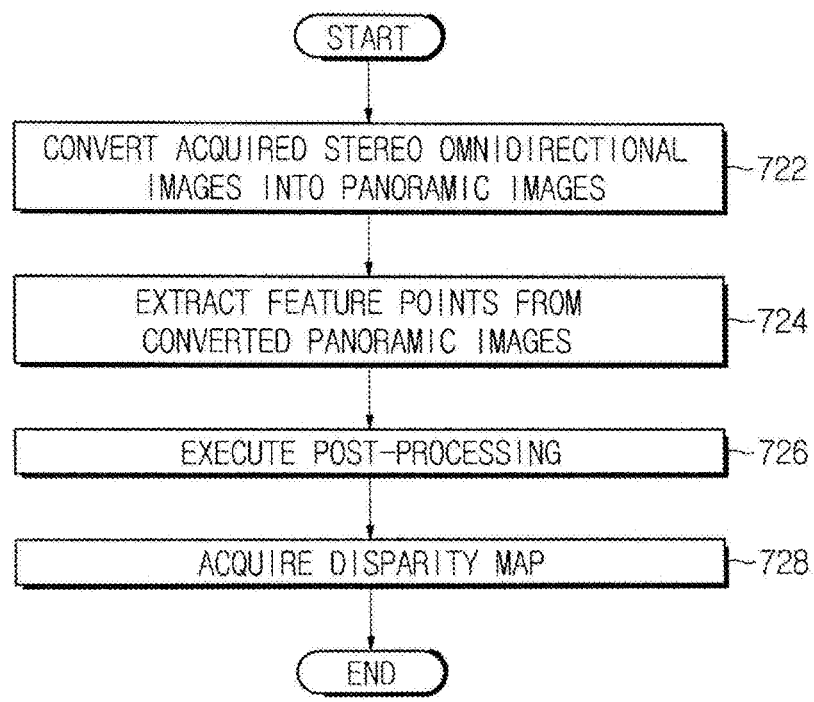

ENDOSCOPE SYSTEM AND CONTROL METHOD THEREOF

CROSS-REFERENCE TO RELATED APPLICATION

This application claims the benefit of Korean Patent Application No. 2013-0022535, filed on Feb. 28, 2013 in the Korean Intellectual Property Office, the entire disclosure of which is incorporated herein by reference.

BACKGROUND

Field

At least one example embodiment of inventive concepts relates to an endoscope system and/or a control method thereof which may be used to examine the inside of an organ or an abdominal cavity.

Description of the Related Art

In general, an endoscope is a medical instrument which is inserted into a human body so that an examiner may examine the inside of an organ (generally, a digestive organ) or an abdominal cavity without an operation or an incision. Early endoscopes were used to simply observe organs within the abdominal cavity of a human body by inserting a thin and long insertion part into the abdominal cavity. Since then, because of development of image processing techniques, images of respective regions within the abdominal cavity of a human body are acquired by a B/W camera, and then lesions at the respective regions may be observed in detail through the acquired images. Further, a color image acquiring device having a high resolution may be substituted for the B/W camera so as to observe lesions in more detail. Further, a chromo endoscope, which photographs the abdominal cavity after dyeing the surface of the abdominal cavity with a specific pigment according to a lesion to be distinguished, may also be used.

As described above, endoscopes have been developed starting from a level providing only a B/W image to a level providing a high-resolution color image or a narrow-band image due to development of image processing techniques.

Such development of endoscopes closely relates to provision of more accurate lesion distinctiveness. Therefore, a 3D endoscope is the most influential as a next generation endoscope technique. Conventional endoscopes provide a 2D image, in which accurate lesion detection may be difficult. For example, detection of a lesion having a similar color to other surrounding tissues but slightly protruding to a height different from the surrounding tissues, may be difficult using only a 2D image. Therefore, research and development is underway for 3D endoscopes capable providing depth information of a photographed region as well as a 2D image.

In order to safely observe a lesion when inserting an endoscope into a digestive organ, such as the esophagus, the stomach, or the large intestine, collision between the endoscope, an object around the endoscope (e.g., the wall of the digestive organ) should be avoided. However, since endoscopes used in current endoscopy provide only a front image captured through an objective lens of a camera mounted at the front end of an insertion part of the endoscope and an examiner (generally, a doctor) operates the endoscope while observing the front image provided from the endoscope, there is a high possibility of collision of the endoscope with the wall of the digestive organ.

SUMMARY

Therefore, it is an aspect of the inventive concepts to provide an endoscope system and/or a control method thereof in which distances between an endoscope and an object around the endoscope (for example, a digestive organ, polyps, or tissues) may be quantitatively calculated using stereo omnidirectional images acquired through a stereo omnidirectional camera mounted on the endoscope, and information regarding avoidance of collision between the endoscope and the object around the endoscope may be provided based on the calculated distance information, so as to facilitate safe operation of the endoscope.

It is another aspect of the present invention to provide an endoscope system and a control method thereof in which distances between an endoscope and an object around the endoscope may be quantitatively calculated using stereo omnidirectional images acquired through the stereo omnidirectional camera mounted on the endoscope, and a 3D grid map of the object (for example, a digestive organ) around the endoscope may be constructed based on the calculated distance information and provided, so as to facilitate accurate diagnosis of the object to be examined.

Additional aspects of the invention will be set forth in part in the description which follows and, in part, will be obvious from the description, or may be learned by practice of the invention.

In accordance with one aspect of the present invention, a control method of an endoscope system includes acquiring plural omnidirectional images of the surroundings of an endoscope using a stereo omnidirectional camera mounted on the endoscope, calculating distances between the endoscope and an object around the endoscope using the acquired plural omnidirectional images, and executing an operation to avoid collision between the endoscope and the object around the endoscope based on the calculated distances.

The calculation of the distances between the endoscope and the object around the endoscope may include executing stereo matching of the acquired plural omnidirectional images and calculating the distances between the endoscope and the object around the endoscope based on information calculated from a disparity map acquired as a result of the stereo matching.

The execution of the stereo matching may include converting the acquired plural omnidirectional images into plural panoramic images, extracting feature points from the converted plural panoramic images, and acquiring the disparity map of the plural panoramic images using a sum of absolute differences (SAD) algorithm.

The execution of the operation to avoid collision may include providing information regarding the moving direction of the endoscope to avoid collision between the endoscope and the object around the endoscope.

In the provision of the information regarding the moving direction of the endoscope to avoid collision, the information regarding the moving direction of the endoscope may be provided so as to move the endoscope in a direction of increasing the shortest distance from among the calculated distances between the endoscope and the object around the endoscope.

In the provision of the information regarding the moving direction of the endoscope to avoid collision, the information regarding the moving direction of the endoscope may be provided so as to move the endoscope in a direction of proceeding to the center of gravity of the cross-section of the object around the endoscope.

The execution of the operation to avoid collision may further include transmitting force and motion to an operating unit to operate the moving direction of the endoscope using force feedback of haptics.

The control method may further include constructing a 3D grid map of the object around the endoscope based on the calculated distances.

The construction of the 3D grid map of the object around the endoscope may include forming plural 3D grids by dividing the object around the endoscope according to a predetermined angle and a predetermined distance, and determining distance information representing each of the plural 3D grids.

The distance information representing each of the plural 3D grids may be the mean distance of points forming each of the plural 3D grids.

In accordance with another aspect of the present invention, an endoscope system includes an endoscope provided with a stereo omnidirectional camera acquiring plural omnidirectional images of the surroundings of the endoscope, and a processor calculating distances between the endoscope and an object around the endoscope using the acquired plural omnidirectional images and executing an operation to avoid collision between the endoscope and the object around the endoscope based on the calculated distances.

The processor may include a stereo matching unit executing stereo matching of the acquired plural omnidirectional images, and a distance calculation unit calculating the distances between the endoscope and the object around the endoscope based on information calculated from a disparity map acquired as a result of the stereo matching.

The stereo matching unit may convert the acquired plural omnidirectional images into plural panoramic images, extract feature points from the converted plural panoramic images, and acquire the disparity map of the plural panoramic images using a sum of absolute differences (SAD) algorithm.

The processor may further include a control signal generation unit generating a control signal to provide information regarding the moving direction of the endoscope to avoid collision between the endoscope and the object around the endoscope.

The control signal generation unit may generate the control signal to provide the information regarding the moving direction of the endoscope so as to move the endoscope in a direction of increasing the shortest distance from among the calculated distances between the endoscope and the object around the endoscope.

The control signal generation unit may generate the control signal to provide the information regarding the moving direction of the endoscope so as to move the endoscope in a direction of proceeding to the center of gravity of the cross-section of the object around the endoscope.

The control signal generation unit may generate a control signal to transmit force and motion to an operating unit to operate the moving direction of the endoscope using force feedback of haptics.

The processor may further include a 3D grid map construction unit constructing a 3D grid map of the object around the endoscope based on the calculated distances.

The 3D grid map construction unit may form plural 3D grids by dividing the object around the endoscope according to a predetermined angle and a predetermined distance, and determine distance information representing each of the plural 3D grids.

The 3D grid map construction unit may determine the mean distance of points forming each of the plural 3D grids as the distance information representing each of the plural 3D grids.

BRIEF DESCRIPTION OF THE DRAWINGS

These and/or other aspects of the example embodiments will become apparent and more readily appreciated from the following description of the embodiments, taken in conjunction with the accompanying drawings of which:

FIG. 13 is a flowchart illustrating a stereo matching process shown in FIG. 12 in detail.

DETAILED DESCRIPTION OF EXAMPLE EMBODIMENTS

Figure 1:
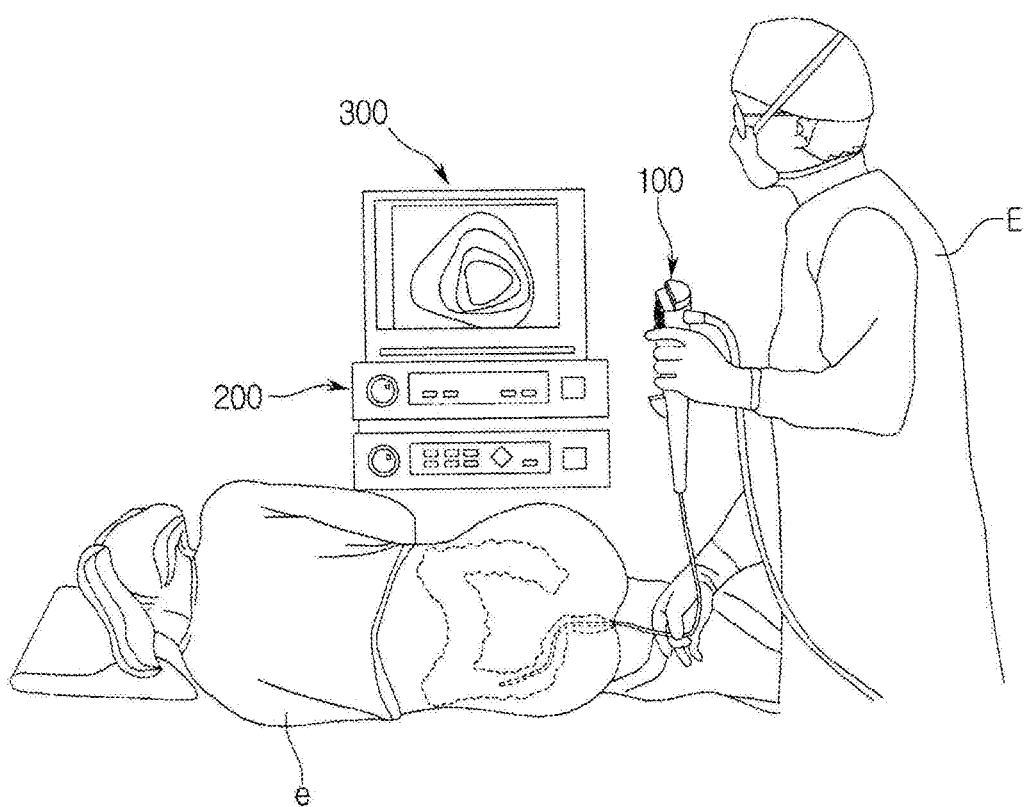
FIG. 1 is a view illustrating execution of colonoscopy using an endoscope system in accordance with at least one example embodiment.

Reference will now be made in detail to example embodiments, which are illustrated in the accompanying drawings, wherein like reference numerals refer to like elements throughout.

Example embodiments will be understood more readily by reference to the following detailed description and the accompanying drawings. The example embodiments may, however, be embodied in many different forms and should not be construed as being limited to those set forth herein. Rather, these example embodiments are provided so that this disclosure will be thorough and complete. In at least some example embodiments, well-known device structures and well-known technologies will not be specifically described in order to avoid ambiguous interpretation.

It will be understood that when an element is referred to as being "connected to" or "coupled to" another element, it can be directly on, connected or coupled to the other element or intervening elements may be present. In contrast, when an element is referred to as being "directly connected to" or "directly coupled to" another element, there are no intervening elements present. Like numbers refer to like elements throughout. As used herein, the term "and/or" includes any and all combinations of one or more of the associated listed items.

It will be understood that, although the terms first, second, third, etc., may be used herein to describe various elements, components and/or sections, these elements, components and/or sections should not be limited by these terms. These terms are only used to distinguish one element, component or section from another element, component or section. Thus, a first element, component or section discussed below could be termed a second element, component or section without departing from the teachings of the example embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including" when used in this specification, specify the presence of stated components, steps, operations, and/or elements, but do not preclude the presence or addition of one or more other components, steps, operations, elements, and/or groups thereof.

Unless otherwise defined, all terms (including technical and scientific terms) used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "below", "beneath", "lower", "above", "upper", and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

FIG. 1 is a view illustrating execution of colonoscopy using an endoscope system in accordance with at least one example embodiment.

As exemplarily shown in FIG. 1, an endoscope system 100 in accordance with at least one example embodiment includes an endoscope 100, a processor 200, and a display 300. When a colonoscopy is carried out, an examiner E, i.e., a doctor, inserts the endoscope 100 into the anus of an examinee e, i.e., a patient, and observes the inside of the large intestine and the end part of the small intestine adjacent to the large intestine of the patient. An image signal regarding an object to be examined (an object to be observed or a region within the abdominal cavity) acquired through a camera attached to the endoscope 100 is transmitted to the processor 200 through a cable. Although FIG. 1 illustrates the endoscope 100 as being connected to the processor 200 through the cable, the endoscope 100 may be wirelessly connected to the processor 200. The processor 200 executes image processing of the image signal transmitted from the endoscope 100 and generates a resultant image (an endoscope image) of various tissues, structures and lesions of the object to be examined (e.g., a digestive organ). The processor 200 displays the resultant image of the object to be examined generated through image processing on a screen of the display 300 connected to the processor 200. Although the processor 200 and the display 300 are shown as independent devices which are physically separated from each other, the processor 200 and the display 300 may be integrated into one body (for example, a personal computer).

Figure 2A:
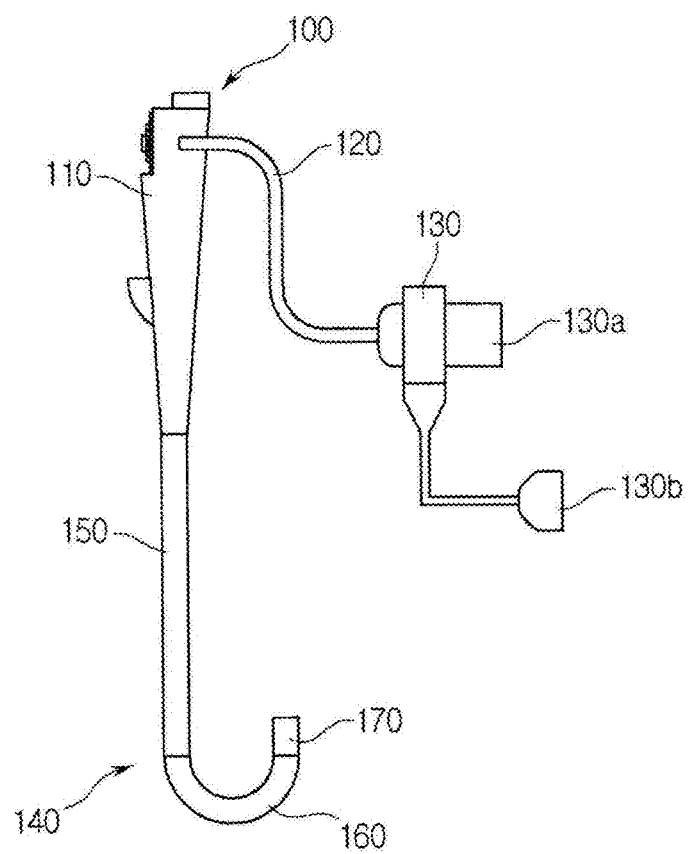
FIG. 2A is a view illustrating the schematic stricture of an endoscope of the endoscope system in accordance with at least one example embodiment.
Figure 2B:
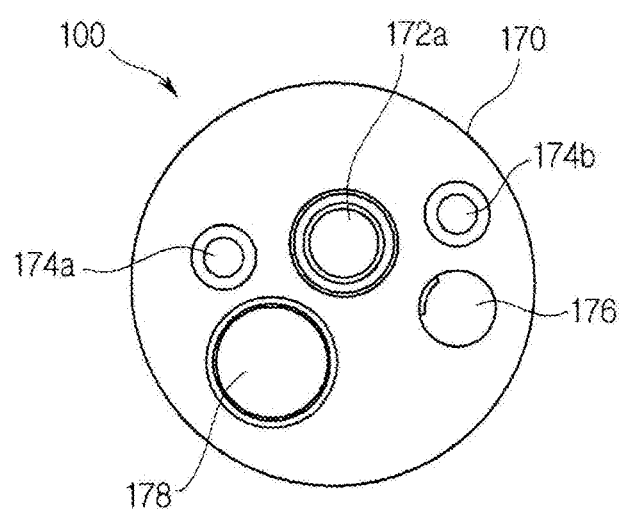
FIG. 2B is a cross-sectional view of a front end part of the endoscope.

FIG. 2A is a view illustrating the schematic stricture of the endoscope of the endoscope system in accordance with at least one example embodiment. FIG. 2B is a cross-sectional view of a front end part of the endoscope.

The endoscope 100 is a device which is inserted into the body of the examinee e and photographs the inside of the organ or the abdominal cavity. As exemplarily shown in FIG. 2A, the endoscope 100 includes an operating unit 110 gripped by the examiner E and for executing manipulation of a curved region of the endoscope and control of a pipe system of the endoscope. The endoscope 100 further includes a universal cable 120 extending from the operating unit 110 and provided with a connector part 130 formed at the front end of the universal cable 120, and an insertion unit 140 connected to the operating unit 110 and inserted into the organ or the abdominal cavity.

One end 130a of the connector unit 130 is connected to an external light source device (not shown) through a designated connector, and the other end 130b of the connector unit 130 is connected to the external processor 200 through a designated connector.

The insertion unit 140 includes a flexible part 150 which may be freely bent, a curved part 160 which may be curved, and a front end part 170 installed at the front end of the curved part 160 and formed of a hard material.

The flexible part 150 includes a helical steel band, a stainless steel wire mesh surrounding the helical steel band, and a covering tube. As such, the flexible part 150 may be manually bent by external force.

The curved part 160 may be formed by connecting a plurality of curved holes (not shown) by a connection member, such as a rivet, so as to be curved with at least one degree of freedom.

As exemplarily shown in FIG. 2B, an objective lens 172a of an endoscope camera 172 (with reference to FIG. 5) focusing the object to be examined (a subject for photography) and two light guide lenses 174a and 174b arranged around the objective lens 172a to irradiate illumination light guided from a light source device (not shown) to the object to be examined may be mounted on the front end part 170. A charge coupled device (CCD, not shown) converting the image of the object to be examined, focused by the objective lens 172a, into an image signal may be arranged in the rear of the objective lens 172a and be connected to the objective lens 172a. The front end part 170 may further include a transreceiver nozzle 176 to inject air to inflate the object to be examined or water to wash the object to be examined, and a treatment tool opening 178 may enter and exit. The treatment tool opening 178 may be for a forceps that extracts tissue in a human body to execute biopsy or for some other operation tool used to execute endoscopy.

An operating handle (not shown) to remotely curve the curved part 160 is installed at the operating unit 110. By manipulating the operating handle, a tightening action and a loosening action are generated by an operating wire (not shown) inserted into the insertion unit 140, and as a result, the curved part 160 may be curved in four directions.

An omnidirectional camera is a camera system which photographs all directions at once using a rotor reflecting mirror, a condenser lens, and an imaging device (an image sensor). Omnidirectional cameras are applied in security facilities, monitoring cameras, robot vision systems, etc. The rotor reflecting mirror may have various shapes, such as a hyperbolic shape, a spherical shape, a conical shape and a combined shape. The imaging device may employ a charge coupled device (CCD) or a complementary metal oxide semiconductor (CMOS). An image (i.e., an omnidirectional image) projected onto the image plane of the imaging device is reflected by the rotor reflecting mirror, and is thus distorted and difficult for a human to observe. Therefore, in order to more accurately observe an image, an external microprocessor converts the coordinates of output of the imaging device and to form a new panoramic image.

The omnidirectional image acquired through the omnidirectional camera provides 2D information regarding the surroundings of the omnidirectional camera. If plural omnidirectional images in different directions captured through plural omnidirectional cameras are used, 3D information regarding the surroundings of the omnidirectional cameras may be acquired. An imaging device including plural omnidirectional cameras is referred to as a stereo omnidirectional camera. By mounting such a stereo omnidirectional camera on an unmanned vehicle or a mobile robot, omnidirectional images captured through the stereo omnidirectional camera may be used in position recognition and map construction of the unmanned vehicle or the mobile robot.

Figure 3:
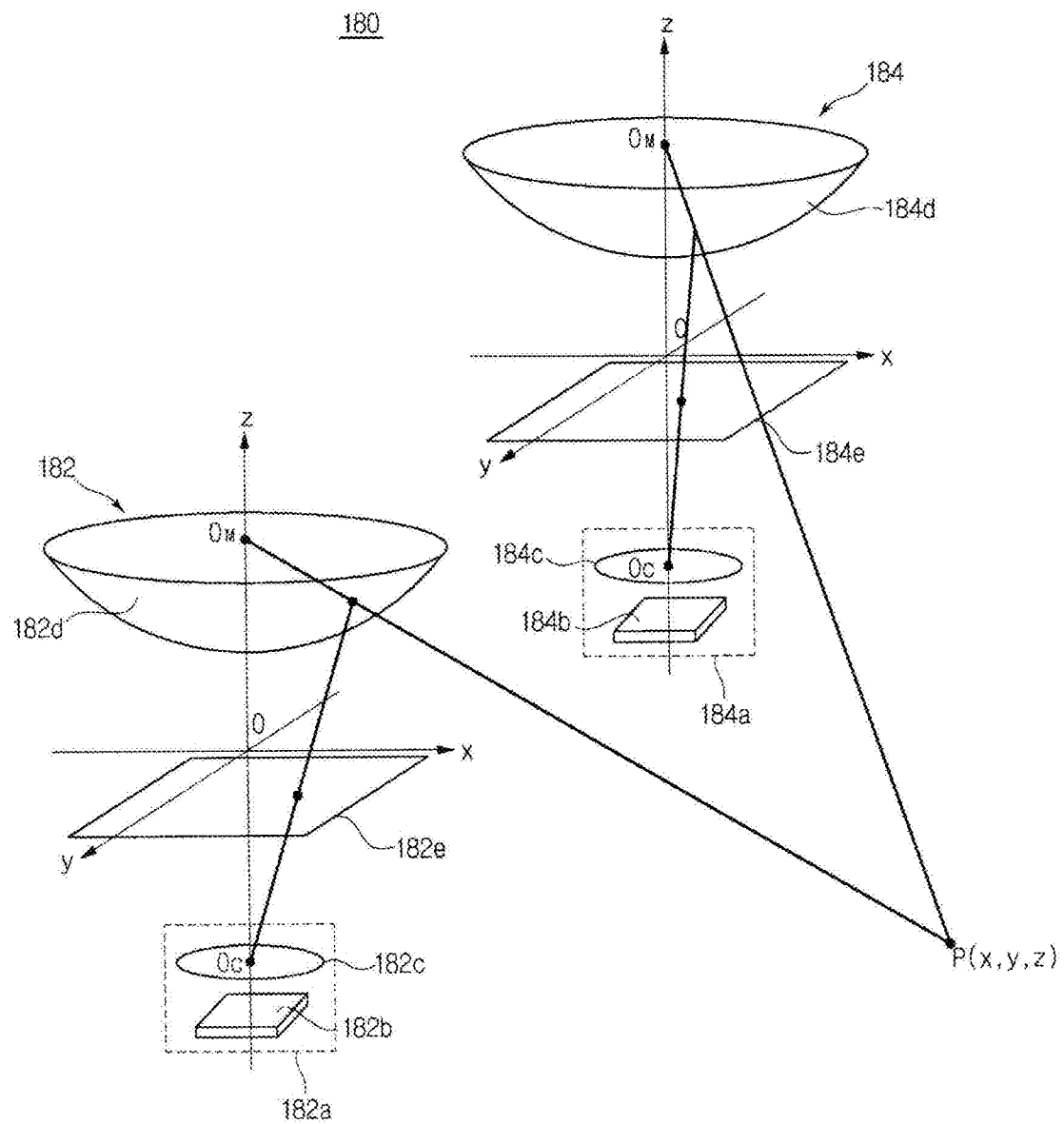
FIG. 3 is a view illustrating the configuration of a stereo omnidirectional camera of the endoscope system in accordance with at least one example embodiment.

FIG. 3 is a view illustrating the configuration of a stereo omnidirectional camera of the endoscope system in accordance with at least one example embodiment of.

As exemplarily shown in FIG. 3, a stereo omnidirectional camera 180 includes a first omnidirectional camera 182 and a second omnidirectional camera 184. The first omnidirectional camera 182 and the second omnidirectional camera 184 are arranged in a line (in the Y-axis direction in FIG. 3), thus forming one stereo omnidirectional camera 180. Although not shown in FIG. 3, the first omnidirectional camera 182 and the second omnidirectional camera 184 may be fixed by a separate fixing device.

The first omnidirectional camera 182 includes a camera module 182*a* including an image sensor 182*b* and a camera lens 182*c*, and a hyperbolic mirror 182*d* which is one example of a robot reflecting mirror. Light incident at an arbitrary point in a 3D space forming an object to be examined (a subject for photograph), i.e., a point of interest P(x, y, z), is reflected by the surface of the hyperbolic mirror 182*d* and is projected onto an image plane 182*e*. Here, the image plane 182*e* corresponds to an XY plane. Further, light incident at the point of interest P(x, y, z) is reflected by the surface of the hyperbolic mirror 182*d* and is transmitted to a central point Oc of the camera lens 182*c* of the camera module 182*a*. The camera module 182*a* converts incident light reflected by the surface of the hyperbolic mirror 182*d* into an electrical signal, thus forming an image signal.

The second omnidirectional camera 184 also includes a camera module 184*a* including an image sensor 184*b* and a camera lens 184*c*, and a hyperbolic mirror 184*d*. Light incident at the arbitrary point in the 3D space forming an object to be examined (a subject for photograph), i.e., the point of interest P(x, y, z), is reflected by the surface of the hyperbolic mirror 184*d* and is projected onto an image plane 184*e*. Here, the image plane 184*e* corresponds to the XY plane. Further, light incident at the point of interest P(x, y, z) is reflected by the surface of the hyperbolic mirror 184*d* and is transmitted to a central point Oc of the camera lens 184*c* of the camera module 184*a*. The camera module 184*a* converts incident light reflected by the surface of the hyperbolic mirror 184*d* into an electrical signal, thus forming an image signal.

Each of the first omnidirectional camera 182 and the second omnidirectional camera 184 captures an image of the surroundings having a viewing angle of 360° (i.e., an omnidirectional image). However, since only 2D information of a subject may be detected from one omnidirectional image, 3D information of the subject may be detected using two omnidirectional images captured at different positions.

Figure 4:
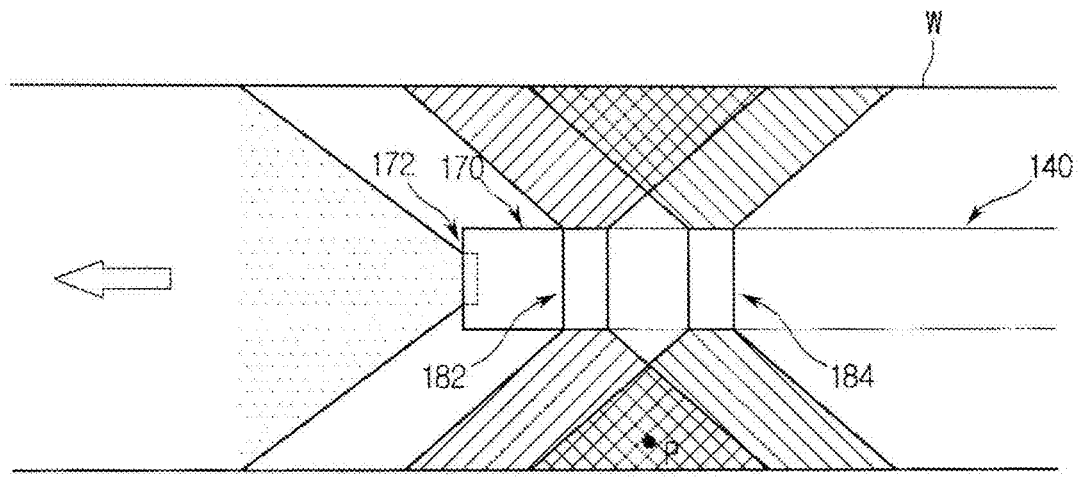
FIG. 4 is a view illustrating the field of view of an endoscope camera mounted on the endoscope and the field of view of the stereo omnidirectional camera.

FIG. 4 is a view illustrating the field of view of the endoscope camera mounted on the endoscope and the field of view of the stereo omnidirectional camera.

As exemplarily shown in FIG. 4, if the insertion unit 140 of the endoscope 100 moves in the direction of the arrow, the field of view (FOV) of the endoscope camera 172 mounted at the front end 170 corresponds to a region expressed by dots of FIG. 4. Therefore, an image of the moving direction of the insertion unit 140 of the endoscope 100, i.e., an image of a front region based on the endoscope camera 172, may be acquired through the endoscope camera 172 mounted at the front end part 170 of the endoscope camera 172. In FIG. 4, W represents the wall of a digestive organ, i.e., an object to be examined.

On the other hand, if the insertion unit 140 of the endoscope 100 moves in the direction of the arrow, the FOV of the first omnidirectional camera 182 mounted at the curved part 160 or the front end part 170 of the endoscope 100 corresponds to a region expressed by diagonal lines originating from the first omnidirectional camera 182 in FIG. 4. Therefore, an omnidirectional image of a portion of the object to be examined, i.e., the digestive organ, (e.g., an image of the wall of a portion of the digestive organ) may be acquired through the first omnidirectional camera 182 mounted at the curved part 160 or the front end part 170 of the endoscope 100.

Further, if the insertion unit 140 of the endoscope 100 moves in the direction of the arrow, the FOV of the second omnidirectional camera 184 mounted at the curved part 160 or the front end part 170 of the endoscope 100 corresponds to a region expressed by diagonal lines originating from the second omnidirectional camera 184 in FIG. 4. Therefore, an omnidirectional image of a portion of the object to be examined, i.e., the digestive organ, (e.g., an image of the wall of a portion of the digestive organ) may be acquired through the second omnidirectional camera 184 mounted at the curved part 160 or the front end part 170 of the endoscope 100.

Here, if an arbitrary point, i.e., a point of interest P, in the 3D space forming the object to be examined (the subject for photography) is present at an intersection region between the FOV of the first omnidirectional camera 182 and the FOV of the second omnidirectional camera 184, as exemplarily shown in FIG. 4, 3D information of the subject for photography may be acquired using the two omnidirectional images acquired through the first omnidirectional camera 182 and the second omnidirectional camera 184.

Figure 5:
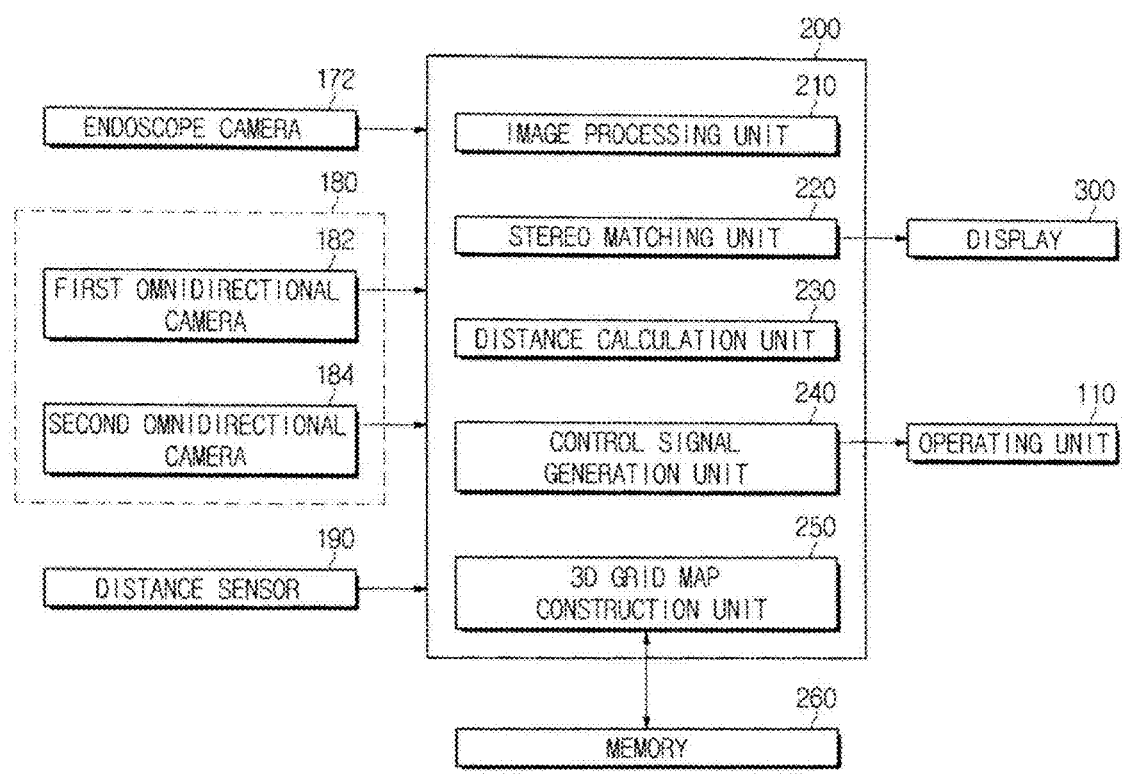
FIG. 5 is a control block diagram of the endoscope system in accordance with at least one example embodiment.

FIG. 5 is a control block diagram of the endoscope system in accordance with at least one example embodiment.

As exemplarily shown in FIGS. 1 and 5, the endoscope system includes the endoscope 100, the processor 200, and the display 300.

The endoscope 100 includes the endoscope camera 172, the stereo omnidirectional camera 180 including the first omnidirectional camera 182 and the second omnidirectional camera 184, a distance sensor 190, and the operating unit 110.

The endoscope camera 172 acquires image information of an object to be examined (e.g., a digestive organ), and transmits the acquired image formation regarding the object to be examined to the processor 200.

The first omnidirectional camera 182 and the second omnidirectional camera 184 of the stereo omnidirectional camera 180 respectively acquire 360° images (i.e., omnidirectional images) of the surroundings around the respective cameras 182 and 184, and transmit the acquired omnidirectional images to the processor 200.

Figure 6:
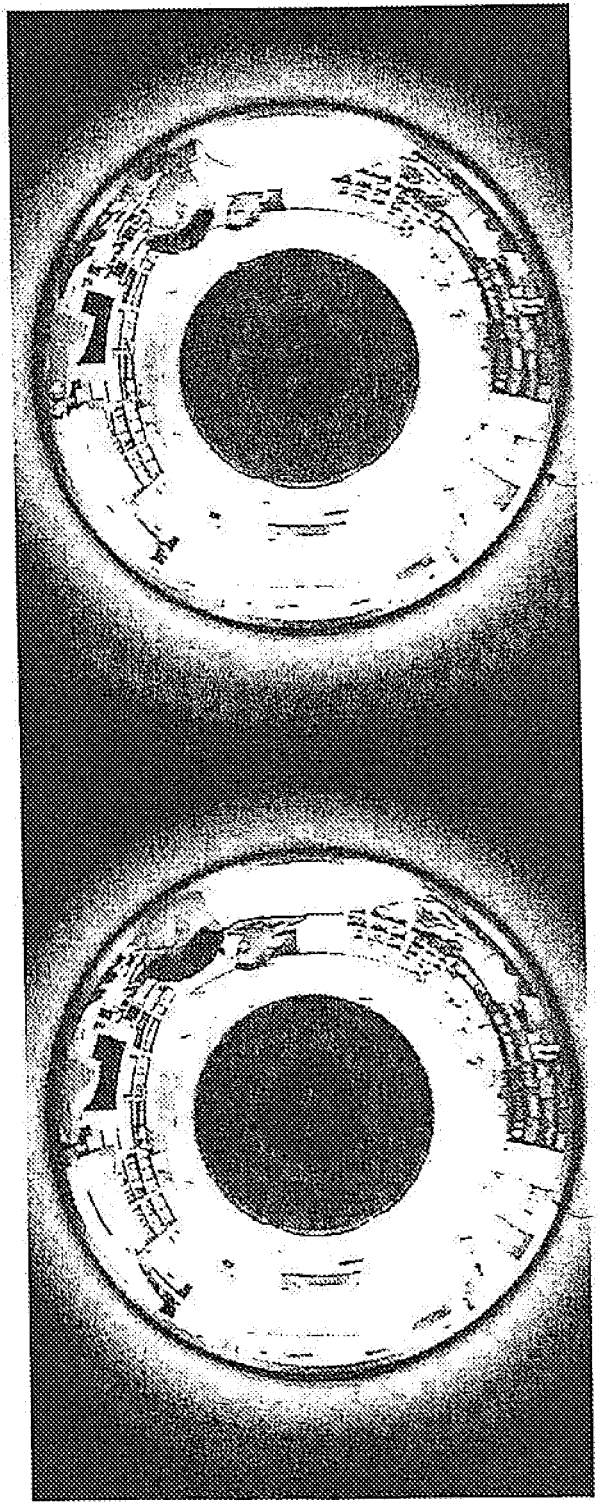
FIG. 6 is a view illustrating omnidirectional images acquired by the stereo omnidirectional camera shown in FIG. 4.

FIG. 6 is a view illustrating omnidirectional images acquired using the stereo omnidirectional camera 180 shown in FIG. 4. As exemplarily shown in FIG. 6, when the stereo omnidirectional camera 180 photographs the surroundings, a first omnidirectional image 402 is acquired through the first omnidirectional camera 182 and a second omnidirectional image 404 is acquired through the second omnidirectional camera 184.

The distance sensor 190 detects position information of the endoscope 100, and transmits the detected position information of the endoscope 100 to the processor 200. The position information of the endoscope 100 acquired through the distance sensor 190 is used in construction of a 3D grid map of the object to be examined.

The processor 200 serves to control the overall operation of the endoscope system, and includes an image processing unit 210, a stereo matching unit 220, a distance calculation unit 230, a control signal generation unit 240, and a 3D grid map construction unit 250.

The image processing unit 210 processes an image input from the endoscope camera 172 so as to output a picture image. Here, image processing may include enlargement, reduction, rotation, movement, editing, and filtering of a captured image.

Prior to a detailed description of operations of the stereo matching unit 220 and the distance calculation unit 230 of the processor 200, hereinafter, a calculation method of distances between the endoscope (or the omnidirectional cameras) and an object to be examined (a subject for photography) will be described with reference to FIGS. 7 to 9.

Figure 7:
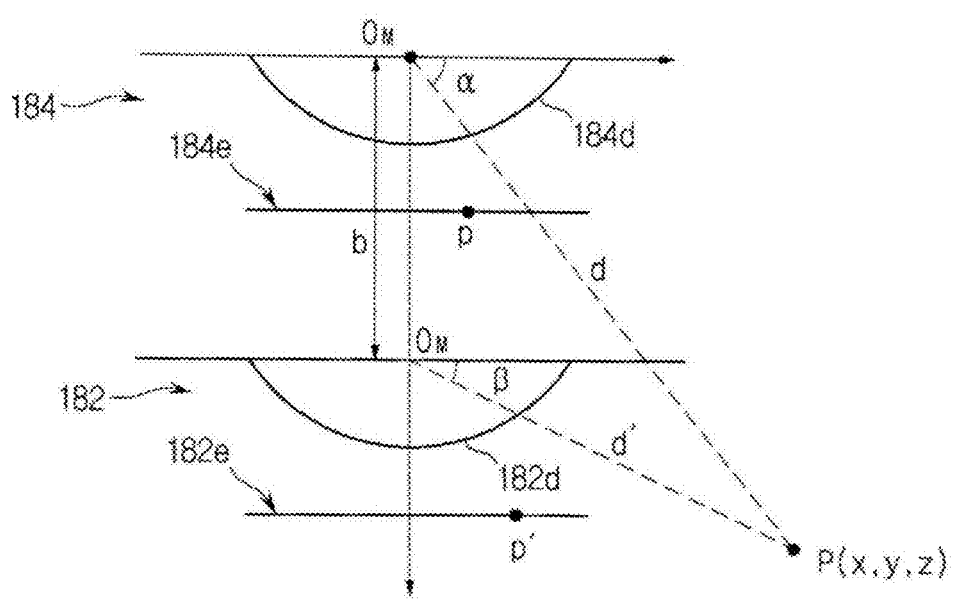
FIG. 7 is a view illustrating distance calculation using the stereo omnidirectional camera.

FIG. 7 is a view illustrating distance calculation using the stereo omnidirectional camera. For convenience of understanding, FIG. 7 illustrates the first omnidirectional camera 182 and the second omnidirectional camera 184 of the stereo omnidirectional camera 180 shown in FIG. 3, 2-dimensionally.

In FIG. 7, b is a distance between the first omnidirectional camera 182 and the second omnidirectional camera 184. For example, the distance b is a base line, or a distance between the central point (focal point) $O_M$ of the hyperbolic mirror 182d of the first omnidirectional camera 182 and the central point (focal point) $O_M$ of the hyperbolic mirror 184d of the second omnidirectional camera 184. A point p' is formed by projecting an arbitrary point P(x, y, z) in the 3D space onto the image plane 182e of the first omnidirectional camera 182. A point p is formed by projecting the arbitrary point P(x, y, z) in the 3D space onto the image plane 184e of the second omnidirectional camera 184. A distance d' is a distance from the first omnidirectional camera 182 to the arbitrary point P(x, y, z) in the 3D space, and distance d is a distance from the second omnidirectional camera 184 to the arbitrary point P(x, y, z) in the 3D space.

The distance d from the second omnidirectional camera 184 to the arbitrary point P(x, y, z) in the 3D space, more specifically, the distance between the central point (focal point) $O_M$ of the hyperbolic mirror 184d of the second omnidirectional camera 184 and the arbitrary point P(x, y, z) in the 3D space may be calculated using Equation 1 below. In the same manner, the distance d' from the first omnidirectional camera 182 to the arbitrary point P(x, y, z) in the 3D space may be calculated.

$$d = \frac{\cos(\beta)}{\sin(\alpha - \beta)} * b \quad \text{[Equation 1]}$$

Here, angle α is an angle formed between a surface passing through the central point $O_M$ of the hyperbolic mirror 184d of the second omnidirectional camera 184 and running parallel with the image plane 184e of the second omnidirectional camera 184 and a line connecting the arbitrary point P to the central point $O_M$ the hyperbolic mirror 184d of the second omnidirectional camera 184. Angle β is an angle formed between a surface passing through the central point $O_M$ of the hyperbolic mirror 182d of the first omnidirectional camera 182 and running parallel with the image plane 182e of the first omnidirectional camera 182 and a line connecting the arbitrary point P to the central point $O_M$ of the hyperbolic mirror 182d of the first omnidirectional camera 182.

In above-described Equation 1, since b is a constant, the distance d between the second omnidirectional camera 184 and the arbitrary point P in the 3D space may be calculated from angles α and β.

Figure 8A:
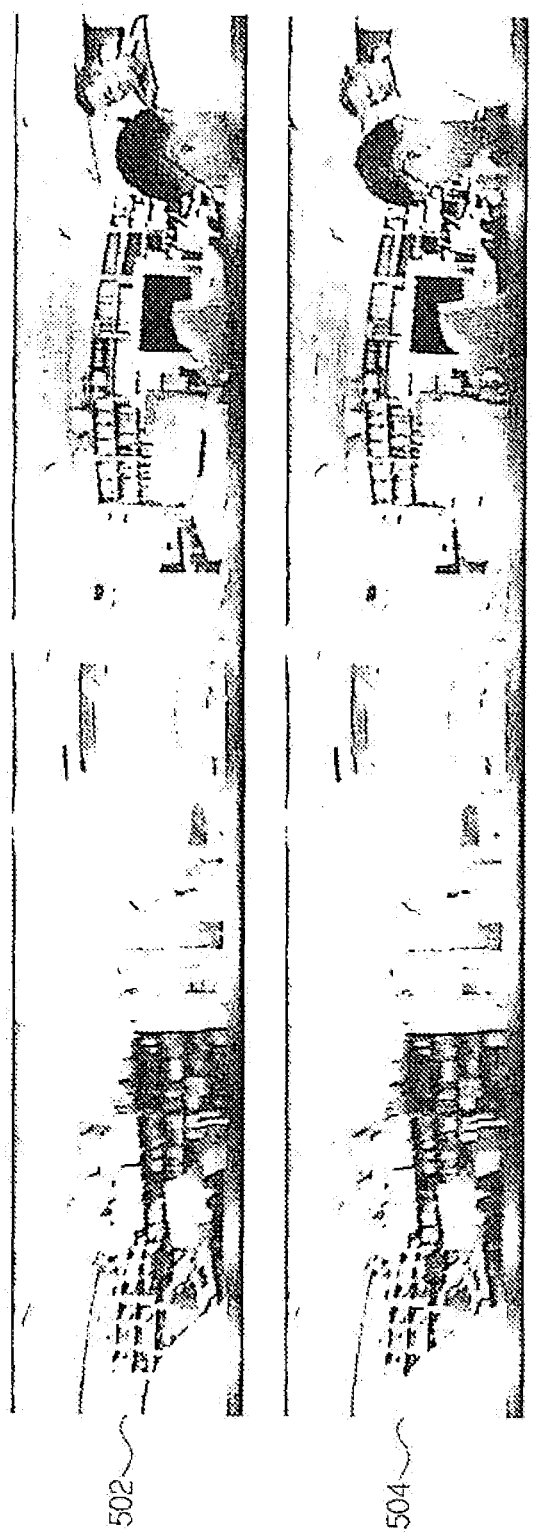
FIG. 8A is a view illustrating resultant images (converted panoramic images) when the two omnidirectional images shown in FIG. 6 are converted into the panoramic images.
Figure 8B:
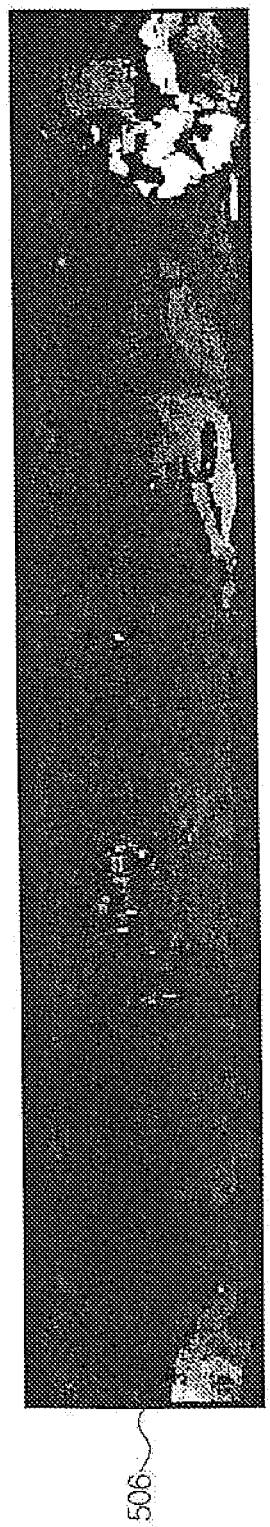
FIG. 8B is a view illustrating a disparity map calculated based on the two panoramic images shown in FIG. 8A.
Figure 9:
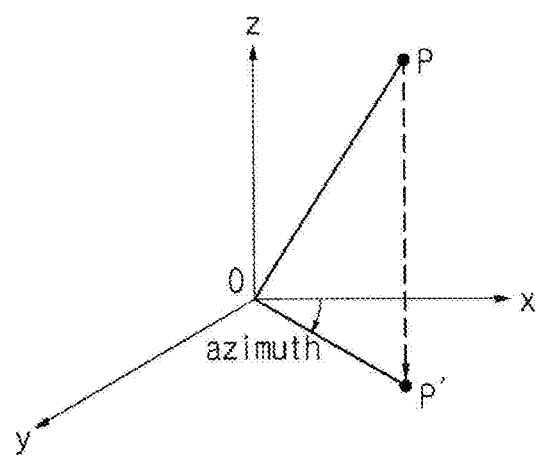
FIG. 9 is a view illustrating the concept of the azimuth of a point of interest.

FIG. 8A is a view illustrating resultant images (converted panoramic images) when the two omnidirectional images shown in FIG. 6 are converted into the panoramic images. FIG. 8B is a view illustrating a disparity map calculated based on the two panoramic images shown in FIG. 8A.

In FIG. 8A, reference numeral 502 represents a panoramic image of a first omnidirectional image 402, i.e., a first panoramic image, and reference numeral 504 represents a panoramic image of a second omnidirectional image 404, i.e., a second panoramic image. Further, in FIG. 8B, reference numeral 506 represents a disparity map calculated through a stereo matching process of the first panoramic image 502 and the second panoramic image 504. In the disparity map 506 shown in FIG. 8B, a subject for photography which is located at a position close to the stereo omnidirectional camera 180 may be relatively lightly shaded, and a subject for photography which is located at a position distant from the stereo omnidirectional camera 180 may be relatively darkly shaded. Using such brightness information (i.e., depth of an image), distances between the stereo omnidirectional camera 180 and subjects for photography may be estimated. Values of angles α and β may be calculated using the disparity map.

Further, the azimuth of the arbitrary point P in the 3D space may be calculated from the panoramic images 502 and 504 shown in FIG. 6. As exemplarily shown in FIG. 9, the azimuth of the arbitrary point P in the 3D space denotes an angle between a reference direction (the X-axis direction) and a line connected from the origin of a coordinate system to a point P' of interest projected onto the same plane (the xy plane) as the reference direction (the X-axis direction), on the assumption that the X-axis direction is defined as the reference direction. If the azimuth of the arbitrary point P in the 3D space is calculated from the panoramic images 502 and 504, the position (x, y, z) of the arbitrary point P in the 3D space may be calculated through Equations 2 to 4 below.

$$x=d^*\cos(\alpha)^*\cos(\text{azimuth}) \quad \text{[Equation 2]}$$

$$y=d^*\cos(\alpha)^*\sin(\text{azimuth}) \quad \text{[Equation 3]}$$

$$z=d^*\sin(\alpha) \quad \text{[Equation 4]}$$

Referring again to FIG. 5, operations of the components of the processor 200 will be described.

The stereo matching unit 220 converts the first and second omnidirectional images 402 and 404 input from the first and second omnidirectional cameras 182 and 184 into the first and second panoramic images 502 and 504, and calculates the disparity map 506 by applying a sum of absolute differences (SAD) algorithm to the two converted panoramic images 502 and 504. As described above, the desired values of angles α and β may be calculated using the disparity map 506 when distances between the stereo omnidirectional camera 180 and a subject for photography are calculated.

The distance calculation unit 230 calculates the distances between the stereo omnidirectional camera 180 and the subject for photography (an object to be examined) and 3D position information, i.e., 3D coordinates P(x, y, z), of the subject for photography (the object to be examined), through above-described Equations 1 to 4.

The control signal generation unit 240 generates a control signal to provide information regarding avoidance of collision between the endoscope 100 and the object to be examined (e.g., the wall of a digestive organ) based on the distance information of the stereo omnidirectional camera 180 and the subject for photography (e.g., distance information d between the endoscope 100 and an object around the endoscope 100), calculated through the distance calculation unit 230. That is, the control signal generation unit 240 generates a control signal to provide information regarding the moving direction of the endoscope 100 to avoid collision so that a user may move the endoscope 100 to the central region of the object to be examined (for example, the esophagus, the stomach, or the large intestine), and transmits the generated control signal to the display 300. The display 300 visually displays information regarding avoidance of collision between the endoscope 100 and the object to be examined on a screen through characters or figures according to the control signal transmitted from the control signal generation unit 240.

Figure 10A:
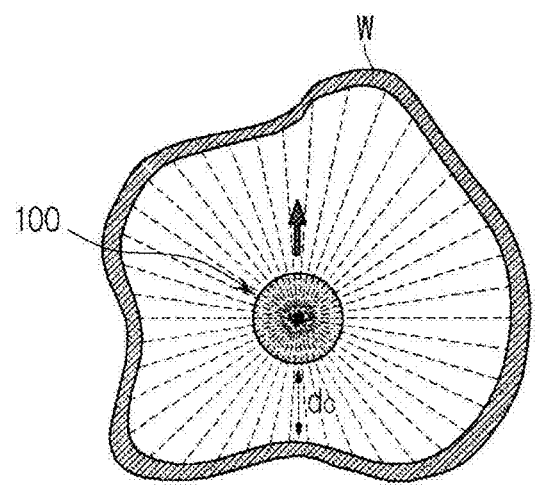
FIGS. 10A and 10B are views exemplarily illustrating visual information provided to avoid collision between the endoscope and an object around the endoscope.
Figure 10B:
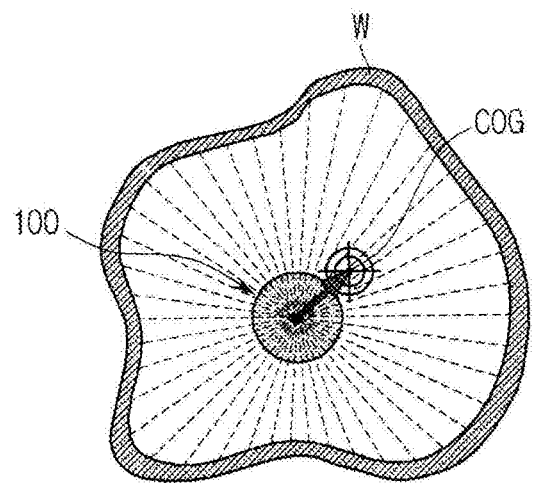

As shown in FIG. 10A, providing information regarding avoidance of collision between the endoscope 100 and the object to be examined (e.g., information regarding the moving direction of the endoscope 100) may allow an examiner E to move the endoscope 100 in a direction (a direction shown by an arrow of FIG. 10A) that increases the shortest distance $d_c$ from among the calculated distances between the endoscope 100 and the object to be examined (the wall W of a digestive organ). Alternatively or additionally, as shown in FIG. 10B, providing information regarding the moving direction of the endoscope 100 may allow an examiner E to move the endoscope 100 in a direction toward the center of gravity (COG) of the cross-section of the object to be examined (a digestive organ). Further, the control signal generation unit 240 generates a control signal to transmit force and motion to the operating unit 110, which may be a joystick, using the distance information d between the stereo omnidirectional camera 180 and the subject for photography and haptics. That is, the control signal genera-tion unit 240 generates and transmits a control signal to cause force in the operating direction of the operating unit 110 such that a user may easily and safely move the endoscope 100 toward the central region of the object to be examined (for example, the esophagus, the stomach, or the large intestine). Through such operation, the operating unit 110 is more easily operated in a direction that increases the distance between the endoscope 100 and the object to be examined.

The 3D grid map construction unit 250 constructs a 3D grid map of the object to be examined based on the distance information between the stereo omnidirectional camera 180 and the subject for photography (or the distance information d between the endoscope and the object to be examined), calculated by the distance calculation unit 230. Since the endoscope 100 passes through a pipe or passage structure, such as the esophagus or the large intestine, the 3D grid map construction unit 250 constructs a 3D grid map of the object to be examined by dividing a region around the endoscope 100 into 3D grids and calculating distance values corresponding to the respective 3D grids. Here, position information of the endoscope 100 for calculating the distance values corresponding to the 3D grids may be acquired by the distance sensor 190. Although FIG. 11 exemplarily illustrates detection of position information of the endoscope 100 for calculating the distance values corresponding to the 3D grids using the distance sensor 190, the position information of the endoscope 100 may be calculated using omnidirectional image information acquired through the stereo omnidirectional camera 180 without use of a separate position sensor.

Figure 11:
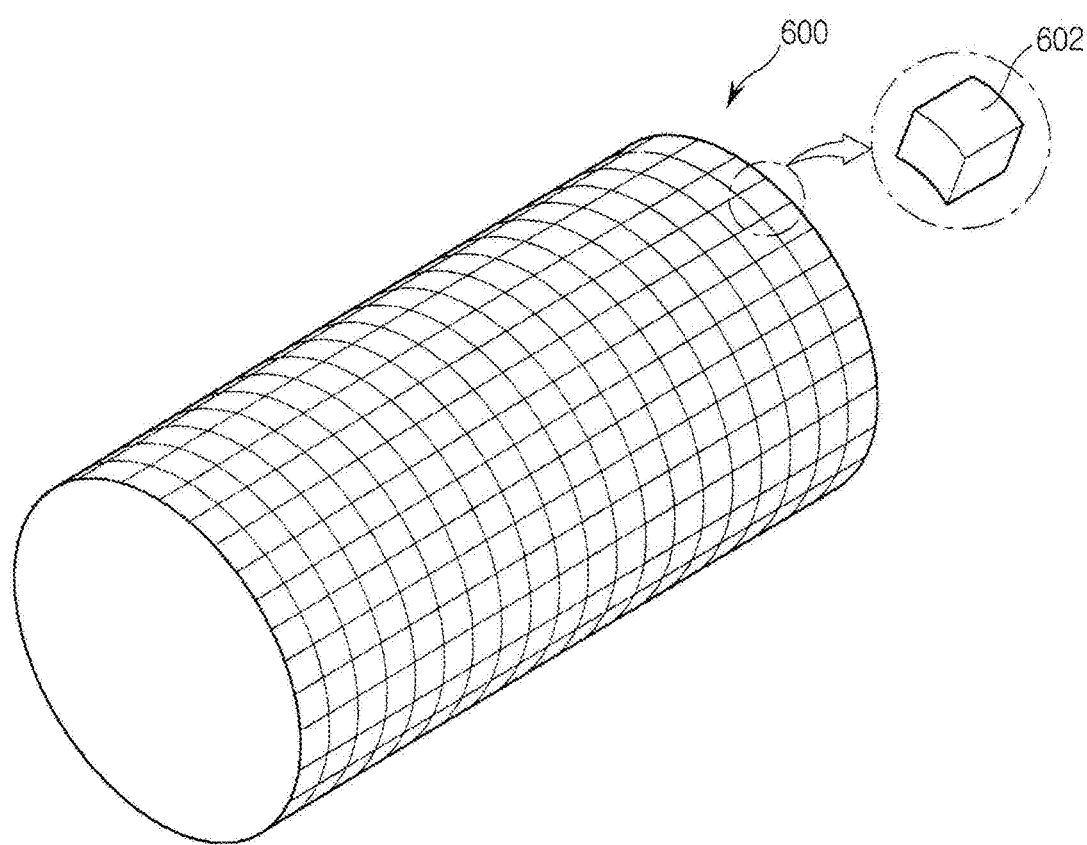
FIG. 11 is a view exemplarily illustrating a 3D grid map regarding an object around the endoscope, constructed based on distance information between the endoscope and the object around the endoscope.

FIG. 11 is a view exemplarily illustrating a 3D grid map regarding an object around the endoscope, constructed based on distance information between the endoscope and the object around the endoscope. FIG. 11 exemplarily illustrates the 3D grid map of an object to be examined having a pipe shape or a cylindrical shape, such as the esophagus or the large intestine. Respective 3D grids 602 are formed by dividing an object around the endoscope 100 according to a desired (or alternatively, predetermined) angle and a desired (or alternatively, predetermined) distance. Distance information representing the respective 3D grids 602 may be set using the mean distance value of points forming the 3D grids 602.

Further, the 3D grid map construction unit 250 may provide a more accurate 3D grip map (image) of the object to be examined by adding color information (RGB values) of stereo omnidirectional images acquired through the stereo omnidirectional camera 180 to a 3D grid map 600 of the object to be examined.

A memory 260 stores the 3D grid map 600 of the object to be examined, constructed by the 3D grid map construction unit 250.

Figure 12:
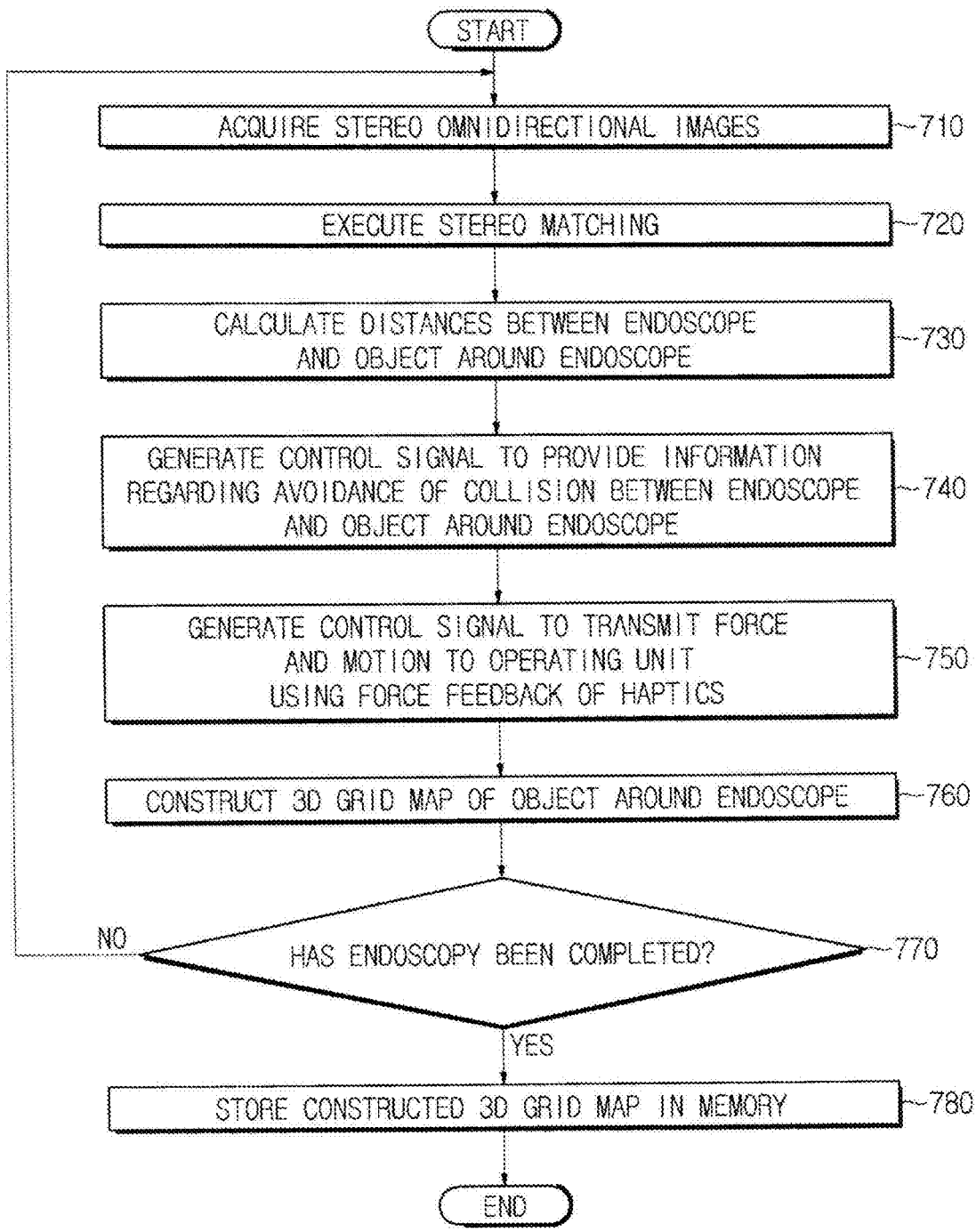
FIG. 12 is a flowchart illustrating a control method of an endoscope system in accordance with at least one example embodiment.

FIG. 12 is a flowchart illustrating a control method of an endoscope system in accordance with at least one example embodiment. FIG. 13 is a flowchart illustrating a stereo matching process shown in FIG. 12.

When an examiner E inserts the endoscope 100 into the abdominal cavity of an examinee, the stereo omnidirectional camera 180 installed at the curved part 160 or the front end part 170 of the endoscope 100 acquires stereo omnidirectional images of an object (e.g., a digestive organ) around the endoscope 100 (Operation 710).

Thereafter, the stereo matching unit 720 within the processor 200 executes stereo matching of first and second omnidirectional images 402 and 404 input from the first and second omnidirectional cameras 182 and 184 of the stereo omnidirectional camera 180 (Operation 720).

Now, such a stereo matching process stated above in Operation 720 will be described in more detail. As exemplarily shown in FIG. 13, the stereo matching unit 720 converts the stereo omnidirectional images 402 and 404 acquired through the stereo omnidirectional camera 180 into panoramic images 502 and 504 (Operation 722). Here, the azimuth of an arbitrary point in a 3D plane, i.e., a point P of interest, may be calculated from the converted panoramic images 502 and 504.

Thereafter, the stereo matching unit 720 extracts feature points from the converted panoramic images 502 and 504 (Operation 724), and executes post-processing of the respective converted panoramic images 502 and 504 (Operation 726).

Next, the stereo matching unit 720 acquires a disparity map 506 between the two panoramic images 502 and 504 by applying a sum of absolute differences (SAD) algorithm to the two converted panoramic images 502 and 504 (Operation 728). Here, the values of angles α and β desired may be calculated using the disparity map 506 when distances between the stereo omnidirectional camera 180 and a subject for photography are calculated.

Thereafter, referring again to FIG. 12, the distance calculation unit 230 within the processor 200 calculates distances between the endoscope 100 and the object around the endoscope 100 and 3D position information of the object around the endoscope 100, i.e., 3D coordinates P(x, y, z), using the values of angles α and β, calculated in Operation 720, the azimuth of the point P of interest, and Equations 1 to 4 described above (Operation 730).

Thereafter, the control signal generation unit 240 within the processor 200 generates a control signal to provide information regarding avoidance of collision between the endoscope 100 and the object around the endoscope 100 (e.g., the wall of a digestive organ) based on distance information d between the endoscope 100 and the object around the endoscope 100 (Operation 740). That is, the control signal generation unit 240 generates and transmits to the operating unit 110 a control signal to provide information regarding the moving direction of the endoscope 100 to avoid collision so that a user may move the endoscope 100 to the central region of an object to be examined (for example, the esophagus, the stomach, or the large intestine) (Operation 740). The display 300 visually displays information regarding avoidance of collision between the endoscope 100 and the object to be examined on a screen through characters and/or figures according to the control signal transmitted from the control signal generation unit 240.

Thereafter, the control signal generation unit 240 within the processor 200 generates a control signal to transmit force and motion to the operating unit 110, which may be a joystick, using the distance information d between the stereo omnidirectional camera 180 and the subject for photography and force feedback of haptics (Operation 750). That is, the control signal generation unit 240 generates and transmits a control signal to the operating unit 110 that causes force in the operating direction of the operating unit 110 so that the user may easily and safely move the endoscope 100 to the central region of the object to be examined (Operation 750). Force and motion are transmitted to the operating unit 110 through such operation, and thus, the operating unit 110 may be more easily operated in a direction that increases the distance between the endoscope 100 and the object to be examined.

Thereafter, the 3D grid map construction unit 250 within the processor 200 constructs a 3D grid map of the object around the endoscope 100 based on the distance information d between the endoscope 100 and the object around the endoscope 100, calculated through the distance calculation unit 230 (Operation 760).

Next, the processor 200 determines whether or not endoscopy has been completed (Operation 770). Upon determining that endoscopy has not been completed ('No' of Operation 770), the processor 200 returns to Operation 710 and thus continuously acquires stereo omnidirectional images of the surroundings of the endoscope 100.

On the other hand, upon determining that endoscopy has been completed ('Yes' of Operation 770), the processor 200 stores the 3D grid map of the object around the endoscope 100, constructed through the 3D grid map construction unit 250, in the memory 260 (Operation 780), and completes an operation to avoid collision between the endoscope 100 and the object around the endoscope 100.

As is apparent from the above description, in an endoscope system and/or a control method thereof in accordance with at least one example embodiment, distances between an endoscope and an object around the endoscope (for example, a digestive organ, polyps, or tissues) may be quantitatively calculated using stereo omnidirectional images acquired through a stereo omnidirectional camera mounted on the endoscope, and information regarding avoidance of collision between the endoscope and the object around the endoscope may be provided based on the calculated distance information, thus facilitating safe operation of the endoscope.

Further, in the endoscope system and/or the control method thereof, the distances between the endoscope and the object around the endoscope may be quantitatively calculated using the stereo omnidirectional images acquired through the stereo omnidirectional camera mounted on the endoscope, and a 3D grid map of the object (for example, a digestive organ) around the endoscope may be constructed based on the calculated distance information and provided, thus facilitating accurate diagnosis of the object to be examined.

Although example embodiments of have been shown and described, it would be appreciated by those skilled in the art that changes may be made in these embodiments without departing from the principles and spirit of the application, the scope of which is defined in the claims and their equivalents.

What is claimed is:

1. A control method of an endoscope system comprising:
   acquiring a plurality of omnidirectional images of surroundings of an endoscope using a stereo omnidirectional camera mounted on the endoscope;
   calculating distances between the endoscope and an object around the endoscope using the acquired plurality of omnidirectional images; and
   executing an operation to avoid collision between the endoscope and the object around the endoscope based on the calculated distances;
   wherein the executing an operation includes providing information regarding a moving direction of the endoscope to avoid collision between the endoscope and the object around the endoscope for moving the endoscope to a central region of the object around the endoscope; and
   constructing a 3D grid map of the object around the endoscope based on the calculated distances,
   wherein the constructing includes, forming a plurality of 3D grids by dividing the object around the endoscope according to a desired angle and a desired distance, and determining distance information representing each of the plurality of 3D grids.

2. The control method according to claim 1, wherein the calculating distances includes, executing stereo matching of the acquired plurality of omnidirectional images, and calculating the distances based on information calculated from a disparity map acquired as a result of the stereo matching.

3. The control method according to claim 2, wherein the executing stereo matching includes, converting the acquired plurality of omnidirectional images into a plurality of panoramic images, extracting feature points from the converted plurality of panoramic images, and acquiring the disparity map of the plurality of panoramic images using a sum of absolute differences (SAD) algorithm.

4. The control method according to claim 1, wherein, in the executing an operation, the information regarding the moving direction of the endoscope is provided so as to move the endoscope in a direction that increases a shortest distance from among the calculated distances between the endoscope and the object around the endoscope.

5. The control method according to claim 1, wherein, in the executing an operation, the information regarding the moving direction of the endoscope is provided so as to move the endoscope in a direction toward a center of gravity of a cross-section of the object around the endoscope.

6. The control method according to claim 1, wherein the executing an operation includes transmitting force and motion to an operating unit that is configured to operate the moving direction of the endoscope using force feedback of haptics.

7. The control method according to claim 1, wherein the distance information representing each of the plurality of 3D grids is a mean distance of points forming each of the plurality of 3D grids.

8. An endoscope system comprising:

an endoscope including a stereo omnidirectional camera configured to acquire a plurality of omnidirectional images of the surroundings of the endoscope; and at least one processor configured to, calculate distances between the endoscope and an object around the endoscope using the acquired plurality of omnidirectional images, and execute an operation to avoid collision between the endoscope and the object around the endoscope based on the calculated distances;

generate a control signal to provide information regarding a moving direction of the endoscope to avoid collision between the endoscope and the object around the endoscope, and move the endoscope to a central region of the object around the endoscope, and construct a 3D grid map of the object around the endoscope based on the calculated distances, form a plurality of 3D grids by dividing the object around the endoscope according to a desired angle and a desired length, and determine distance information representing each of the plurality of 3D grids.

9. The endoscope system according to claim 8, wherein the at least one processor is further configured to, execute stereo matching of the acquired plurality of omnidirectional images; and calculate the distances between the endoscope and the object around the endoscope based on information calculated from a disparity map acquired as a result of the stereo matching.

10. The endoscope system according to claim 9, wherein the at least one processor is further configured to, convert the acquired plurality of omnidirectional images into a plurality of panoramic images, extract feature points from the converted plurality of panoramic images, and acquire the disparity map of the plurality of panoramic images using a sum of absolute differences (SAD) algorithm.

11. The endoscope system according to claim 9, wherein the at least one processor is configured to generate the control signal to provide the information regarding the moving direction of the endoscope so as to move the endoscope in a direction that increases a shortest distance from among the calculated distances between the endoscope and the object around the endoscope.

12. The endoscope system according to claim 8, wherein the at least one processor is further configured to generate the control signal to provide the information regarding the moving direction of the endoscope so as to move the endoscope in a direction toward a center of gravity of a cross-section of the object around the endoscope.

13. The endoscope system according to claim 8, wherein the at least one processor is further configured to generate a control signal to transmit force and motion to an operating unit that is configured to operate the moving direction of the endoscope using force feedback of haptics.

14. The endoscope system according to claim 8, wherein the at least one processor is further configured to determine a mean distance of points forming each of the plurality of 3D grids as the distance information representing each of the plurality of 3D grids.

* * * * *